United States Patent
Park et al.

(10) Patent No.: US 7,753,846 B2
(45) Date of Patent: Jul. 13, 2010

(54) APPARATUS FOR MEASURING SKIN MOISTURE CONTENT AND IT'S OPERATION METHOD

(75) Inventors: Jeong Je Park, Daegu (KR); Hong Sig Kim, Seongnam-si (KR); Woo Young Jang, Seoul (KR); Jae Chan Park, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 348 days.

(21) Appl. No.: 11/892,428

(22) Filed: Aug. 22, 2007

(65) Prior Publication Data
US 2008/0051643 A1 Feb. 28, 2008

(30) Foreign Application Priority Data
Aug. 22, 2006 (KR) .................. 10-2006-0079524

(51) Int. Cl.
A61B 5/00 (2006.01)
A61B 5/05 (2006.01)

(52) U.S. Cl. .................. 600/307; 600/306; 600/547

(58) Field of Classification Search .................. 600/306, 600/300, 345–366, 372, 382, 384, 307, 547
See application file for complete search history.

(56) References Cited

U.S. PATENT DOCUMENTS

| | | | |
|---|---|---|---|
| 4,013,065 A | | 3/1977 | Copeland et al. |
| 4,480,921 A | * | 11/1984 | Leveque et al. ............. 356/434 |
| 4,483,619 A | * | 11/1984 | Leveque et al. ............. 356/434 |
| 4,711,244 A | * | 12/1987 | Kuzara ....................... 600/306 |
| 4,966,158 A | | 10/1990 | Honma et al. |
| 5,353,802 A | | 10/1994 | Ollmar et al. |
| 5,738,107 A | | 4/1998 | Martinsen et al. |
| 5,795,293 A | * | 8/1998 | Carim et al. ................ 600/372 |

(Continued)

FOREIGN PATENT DOCUMENTS

JP 6-66619 3/1994

(Continued)

OTHER PUBLICATIONS

Extended European Search Report, mailed Jan. 21, 2008 and issued in corresponding European Patent Application No. 07114519.7-2319.

(Continued)

*Primary Examiner*—Charles A Marmor, II
*Assistant Examiner*—Navin Natnithithadha
(74) *Attorney, Agent, or Firm*—Staas & Halsey LLP

(57) ABSTRACT

An apparatus for measuring skin moisture content, the apparatus including: an electrode unit comprising a reference (R) electrode, a current (C) electrode, and a measuring (M) electrode; an operational amplifier including an inverting input terminal that is supplied to a first voltage and connects with the R electrode, and an output terminal that connects with the C electrode; a switch controlling a connection between the output terminal and the C electrode; and a comparison control unit comparing the first voltage with a voltage at the output terminal, and controlling the switch to connect the output terminal and the C electrode when the voltage at the output terminal is less than or equal to a value that is acquired by multiplying the first voltage and a predetermined constant.

13 Claims, 8 Drawing Sheets

U.S. PATENT DOCUMENTS

| | | | |
|---|---|---|---|
| 5,944,661 A * | 8/1999 | Swette et al. | 600/345 |
| 6,032,060 A * | 2/2000 | Carim et al. | 600/372 |
| 6,119,038 A * | 9/2000 | Cook | 607/3 |
| 6,442,422 B1 * | 8/2002 | Duckert | 600/547 |
| 2003/0222662 A1 * | 12/2003 | Geisel | 324/664 |
| 2005/0159655 A1 | 7/2005 | Kao | |
| 2008/0051643 A1 * | 2/2008 | Park et al. | 600/306 |
| 2008/0091091 A1 * | 4/2008 | Jang et al. | 600/306 |
| 2008/0177198 A1 * | 7/2008 | Jang et al. | 600/547 |

FOREIGN PATENT DOCUMENTS

| | | |
|---|---|---|
| JP | 9-75316 | 3/1997 |
| JP | 2003-169788 | 6/2003 |
| JP | 2004-312486 | 11/2004 |
| JP | 2005-52227 | 3/2005 |

OTHER PUBLICATIONS

Office Action mailed on Apr. 4, 2008 and issued in corresponding Korean Patent Application No. 10-2006-0079524.

* cited by examiner

APPARATUS FOR MEASURING SKIN MOISTURE CONTENT AND IT'S OPERATION METHOD

CROSS-REFERENCE TO RELATED APPLICATION

This application claims the benefit of Korean Patent Application No. 10-2006-0079524, filed on Aug. 22, 2006, in the Korean Intellectual Property Office, the disclosure of which is incorporated herein by reference.

BACKGROUND

1. Field

Embodiments relate to an apparatus for measuring skin moisture content and it's operation method. And more specifically it is about an apparatus for measuring skin moisture content and it's operation method which can prevent measurement errors that may occur when a current (C) electrode contacts with a user's skin before a reference (R) electrode, by measuring the user's skin moisture content only when a voltage at an output terminal of an operational amplifier is less than or equal to a value that is acquired by multiplying the voltage, which is supplied to a non-inverting input terminal of the operational amplifier by a predetermined constant.

2. Description of the Related Art

As many people become interested in beauty, an interest in skin care has also increased. A desire for a healthy skin affects not only beauty-related businesses, but also affects the growth of medical-related businesses since people need to protect their skin from ultraviolet rays that have become stronger due to the destruction of the ozone layer and various types of pollutions.

Skin is an organ of the integumentary system made up of multiple layers of epithelial tissues. Main functions of skin are protection against pathogens, harmful substances and the cold, waterproofing, temperature regulation, and the like. One of the most critical elements to enable the proper performance of the functions of skin is moisture content in a stratum corneum. Moisture content in the stratum corneum is generally referred to as skin moisture content. Maintaining proper moisture content in the stratum corneum enables the performing of basic functions of skin such as protection against harmful substances, and preventing excessive evaporation of skin moisture.

In view of skin care, skin moisture content is also considered as an essential element. Accordingly, fundamental to skin care is skin moisture management.

According to a conventional art, an electrical measurement method, an optical measurement method, and a method using a magnetic resonance imaging (MRI) are conventional methods of measuring skin moisture content. The electrical measurement method is widely used. More particularly, a method of measuring skin moisture content by measuring susceptance, i.e. an alternating current (AC) component of admittance of three electrodes, i.e. a reference (R) electrode, a current (C) electrode and a measuring (M) electrode, using a sinusoidal wave of low frequency is mainly used.

In the conventional method of measuring skin moisture content, measurement errors may occur in an order of contact by each electrode with the user's skin. Specifically, when the R electrode is the first electrode to contact with the user's skin and the C electrode subsequently contacts with the user's skin, skin moisture content may be measured by detecting a normal current signal from the user's skin via the M electrode.

However, when the C electrode contacts with the user's skin before the R electrode, noise may occur in the current signal detected via the M electrode due to a high voltage, which is supplied to the C electrode. Thus, the skin moisture content may not be accurately measured. Specifically, since noise may occur depending upon an order which a user contacts each electrode with the skin, the skin moisture content may not be accurately or consistently measured.

When noise occurs, often generating an error in measuring skin moisture content, a user may not make appropriate skin care choices, such as purchasing cosmetics unsuitable for the user's skin type based on an incorrect measurement value of skin moisture content, and the like.

Thus, an apparatus for measuring a user's skin moisture content accurately and consistently regardless of an order of contact by each electrode with the skin of the user, is required.

SUMMARY

Additional aspects and/or advantages will be set forth in part in the description which follows and, in part, will be apparent from the description, or may be learned by practice of the invention.

An aspect provides an apparatus for measuring skin moisture content and the method, which can prevent measurement errors that may occur due to an order of contact by each electrode with the user's skin, by detecting noise that may occur when the electrodes contact with a the user's skin in an order of a reference (R) electrode, a current (C) electrode, and a measuring (M) electrode that contact with a user's skin, and measuring the user's skin moisture content when the occurrence of the noise disappears.

An aspect also provides an apparatus for measuring skin moisture content and it's operation method, which can accurately measure skin moisture content by automatically selecting a starting point in time for measurement and eliminating a need for an input of the starting time for measuring skin moisture content, and by maintaining a predetermined measurement time while eliminating a need for installing another device such as a switch for notification of the starting time, since the skin moisture content is measured by detecting noise that occurs depending upon an order of contacting each electrode with the skin.

According to an aspect of the embodiments, there is provided an apparatus of measuring skin moisture content, the apparatus including: an electrode unit including a reference (R) electrode, a current (C) electrode, and a measuring (M) electrode; an operational amplifier including an inverting input terminal that is supplied to a first voltage and connects with the R electrode, and an output terminal that connects with the C electrode; a switch controlling a connection between the output terminal and the C electrode; and a comparison control unit comparing the first voltage with a voltage at the output terminal, and controlling the switch to connect the output terminal and the C electrode when the voltage at the output terminal is less than or equal to a value that is acquired by multiplying the first voltage and a predetermined constant.

According to another aspect of the embodiments, there is provided a method of measuring skin moisture content using a skin moisture content measurement apparatus including an R electrode, a C electrode, an M electrode, and an operational amplifier, the method including: controlling a switch to release a connection between an output terminal of the operational amplifier and the C electrode; supplying a first voltage to an inverting input terminal of the operational amplifier; comparing a value, acquired by multiplying the first voltage and a predetermined constant, with a voltage at the output terminal of the operational amplifier; and controlling the switch to connect the output terminal and the C electrode when the voltage at the output terminal is less than or equal to the value that is acquired by multiplying the first voltage and the predetermined constant.

Additional and/or other aspects and advantages of the embodiments will be set forth in part in the description which follows and, in part, will be obvious from the description, or may be learned by practice of the invention.

BRIEF DESCRIPTION OF THE DRAWINGS

The above and/or other aspects and advantages of the embodiment will become apparent and more readily appreciated from the following detailed description, taken in conjunction with the accompanying drawings of which.

DETAILED DESCRIPTION OF THE EMBODIMENTS

Figure 1:
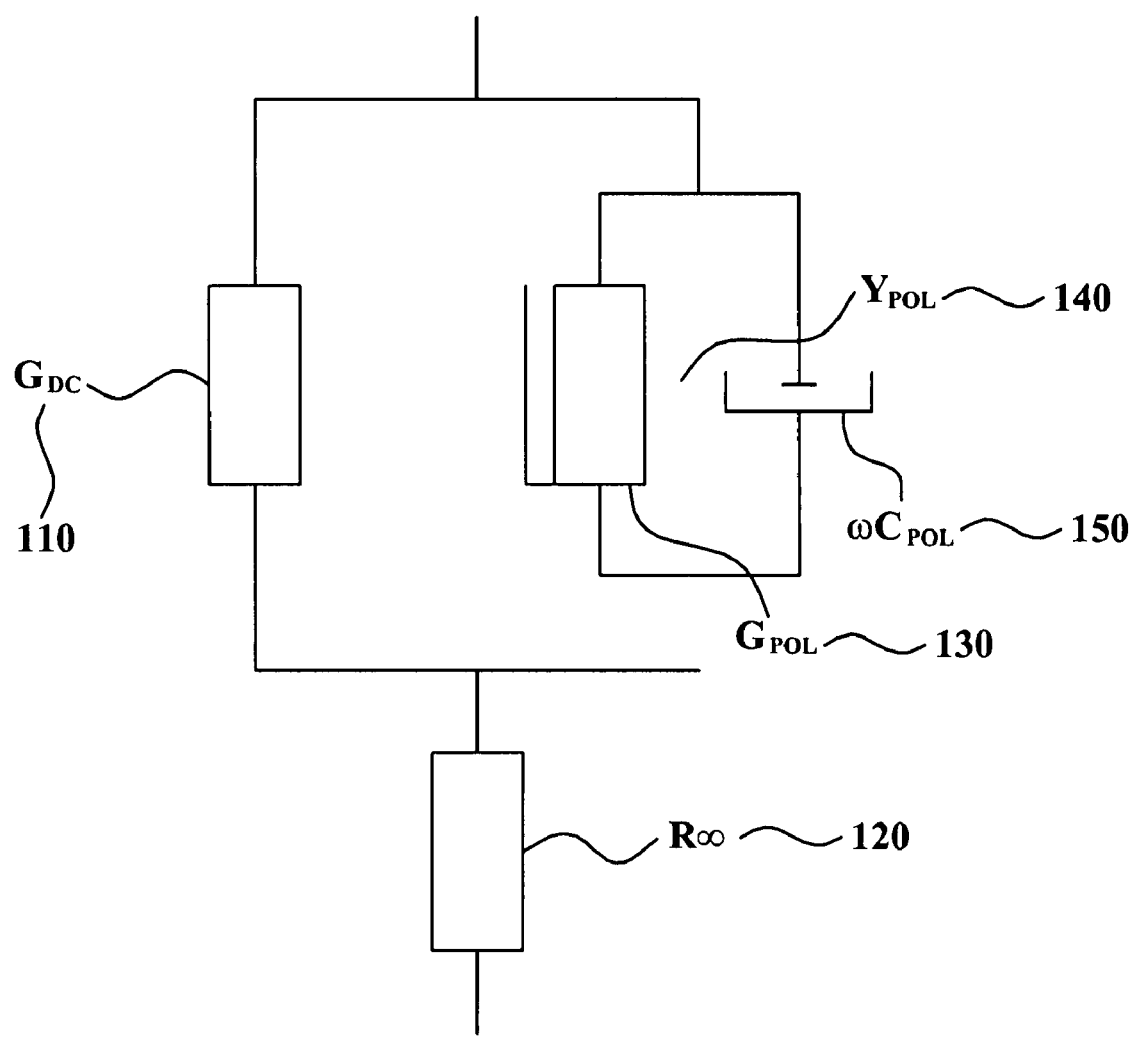
FIG. 1 is a circuit diagram illustrating an electrically modeled biological structure of skin.

Reference will now be made in detail to exemplary embodiments, examples of which are illustrated in the accompanying drawings, wherein like reference numerals refer to the like elements throughout. The exemplary embodiments are described below in order to explain the embodiment by referring to the figures.

An apparatus for measuring skin moisture content according to an embodiment may be embodied as any portable devices, e.g. a mobile communication terminal, a personal digital assistance (PDA), a portable game device, an Moving Picture Experts Group Audio Layer 3 (MP3) player, a portable multimedia player (PMP), a Digital Multimedia Broadcasting (DMB) terminal, a notebook, and the like. Specifically, the apparatus for measuring skin moisture content may be embodied as a partial configuration of the portable devices or may be independently embodied as a single product, instead of being embodied as the partial configuration of the portable devices.

The apparatus for measuring skin moisture content according to an embodiment may measure skin moisture content by electrically modeling a biological structure of skin. Hereinafter, a measurement principle of measuring skin moisture content according to electrical modeling of the skin will be described with reference to FIGS. 1 through 3 and an apparatus for measuring skin moisture content and it's operation method according to the embodiment will be described with reference to FIGS. 4 through 6.

Figure 2:
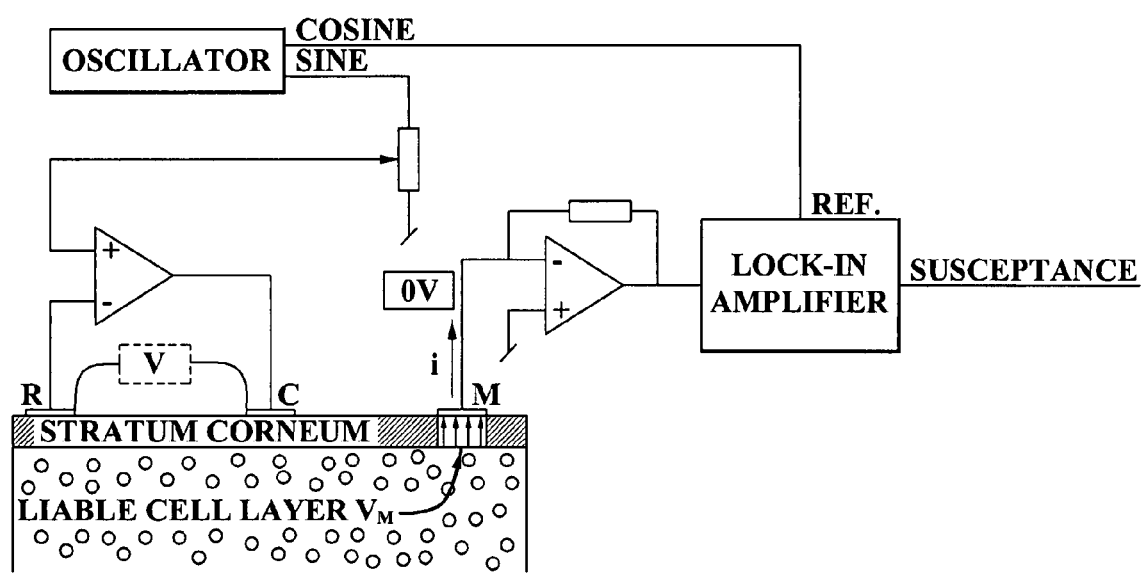
FIG. 2 is a block diagram illustrating a measurement principle of measuring skin moisture content.
Figure 3:
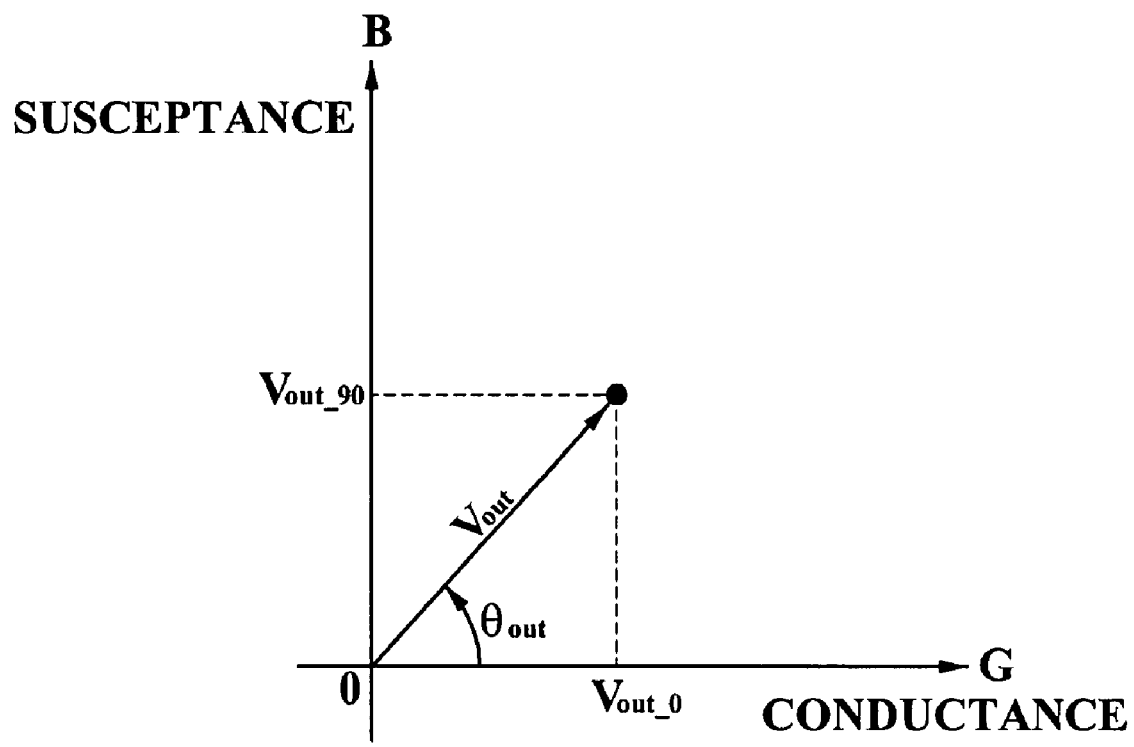
FIG. 3 is a diagram illustrating a graph of admittance by a skin moisture content measurement result.

FIG. 1 is a circuit diagram illustrating an electrically modeled biological structure of skin;

FIG. 2 is a block diagram illustrating a measurement principle of measuring skin moisture content;

FIG. 3 is a diagram illustrating a graph of admittance by a skin moisture content measurement result;

To electrically measure the skin moisture content, it is required to electrically model the biological structure of the skin. FIG. 1 illustrates an electrically modeled biological structure of skin by using a Yamamoto-Yamamoto model, 'The measurement principle for evaluating the performance of drugs and cosmetics by skin impedance' in Med. & Biol. Eng. & Comput. 1978. The Yamamoto-Yamamoto model reinterpreted a Cole-Cole model, 'Dispersion and absorption in dielectrics', in J. Soc. Cosmet. Chem. 1941.

Referring to FIG. 1, $G_{DC}$ 110 generally indicates a sweat gland activity of a stratum corneum. $R_\infty$ 120 indicates a value which is acquired by electrically modeling a liable cell from a bottom of a stratum corneum to a dermis. The $R_\infty$ 120 is direct current (DC) dominant, $Y_{POL}$ 140 indicates an admittance component due to a polarizing phenomenon, and is alternating current (AC) dominant. A $\omega C_{POL}$ 150 component is known to model the skin moisture content of the stratum corneum. Accordingly, when measuring the skin moisture content of the stratum corneum, removing an effect of the R∞ 120 and the $G_{DC}$ 110 may become an important issue.

To measure only the $\omega C_{POL}$ 150 component, only susceptance which is an AC component of the admittance component is used to be measured. For this, an analog lock-in amplifier may be utilized.

Specifically, the $R_\infty$ may be assumed to be a conductor as shown in FIG. 2. When a constant voltage signal(V) of a regular frequency, for example, $\omega=2\pi f$, is supplied to a human body by using the $R_\infty$ as the conductor, a current, which reacts to an impedance of the stratum corneum, may be measured through the conductor of a liable cell layer. In this instance, the stratum corneum closely attaches to a measurement electrode. The admittance of the stratum corneum of a measured area may be measured by using the current.

A response signal which converts the measured current to a voltage is represented as $$V\text{sig} = |V\text{sig}|\sin(\omega rt + \theta\text{sig}) \quad \text{[Equation 1]}$$

Also, an out-phase reference signal having a phase difference of 90° to be synchronous with the response signal is represented as $$V_{L\_90} = |V_{L\_90}|\cos(\omega_{L\_90}t + \theta_{ref\_90}) \quad \text{[Equation 2]}$$

In this case, an in-phase reference signal having a phase difference of 0° to be synchronous with the response signal may be represented as, $$V_{L\_O} = |V_{L\_0}|\sin(\omega_{L\_0}t + \theta_{ref\_0}) \quad \text{[Equation 3]}$$

In this instance, when synchronizing the response signal and the reference signal having the phase difference of 90° using a multiplier, a signal may be generated by $$V_{PSD} = |V sig||V_{L\_90}|\sin(\omega rt + \theta sig)\cos(\omega L\_90t + \theta_{ref\_90}) \quad \text{[Equation 4]}$$
$$= 1/2|V sig||V_{L\_90}|\{\sin([\omega r - \omega_{L\_90}]t +$$
$$\theta sig - \theta_{ref\_90}) - \sin([\omega r + \omega_{L\_90}]t +$$

-continued $$\theta sig + \theta_{ref\_90})\}$$

Also, when the signal passes through a low-pass filter (LPF), the AC component is removed from the signal. Accordingly, $V_{PSD}$ becomes '0'.

However, when frequencies of the reference signal and the response signal are identical, i.e. $\omega r = \omega_{L\_90}$, an output of the LPF may be represented as $$Vout\_90 = \tfrac{1}{2}|Vsig||V_{L\_90}|\sin(\theta sig - \theta_{ref\_90})$$ [Equation 5]

Also, when synchronizing the in-phase reference signal and the response signal by a method as described above, it may be given by $$Vout\_0 = \tfrac{1}{2}|Vsig||V_{L\_0}|\cos(\theta sig - \theta_{ref\_0})$$ [Equation 6]

Also, when $|Vsig||V_L|=Vout$ and $\theta sig - \theta ref = \theta out$ to simplify the equations with respect to the Vout__90 and Vout__0, it may be arranged by $$V_{PSD\_filtered\_0} = \tfrac{1}{2}Vout\cos(\theta out).$$ [Equation 7]

The equations with respect to the Vout__90 and Vout__0, i.e. Equation 5 and Equation 6 designate a conductivity signal which is generated by supplying a constant AC voltage and measuring the current. Accordingly, the admittance is measured. FIG. 3 illustrates a graph of the admittance. In FIG. 3, G designates conductance, and B designates susceptance. When G and an in-phase synchronous signal are combined, G may be measured. When B and a quadrature-phase synchronous signal are combined, B may be measured.

As described above, skin moisture content may be measured from a susceptance that is measured via an out-phase signal. In this instance, to measure only skin moisture content, a conductance component which reflects an effect of a sweat gland of the stratum corneum is required to be removed. Accordingly, only the susceptance may be measured by using the out-phase synchronous signal. According to an embodiment, a method of measuring the skin moisture content may be applied by measuring the susceptance which varies over time.

A method of measuring skin moisture content by measuring a susceptance and a method of measuring sweat gland activity of skin by measuring conductance have been described with FIGS. 1 through 3, and may be applied as a configuration and operational principle of an apparatus for measuring skin moisture content according to an embodiment and it's operation method, which will be described from FIGS. 4 to 6.

Figure 4:
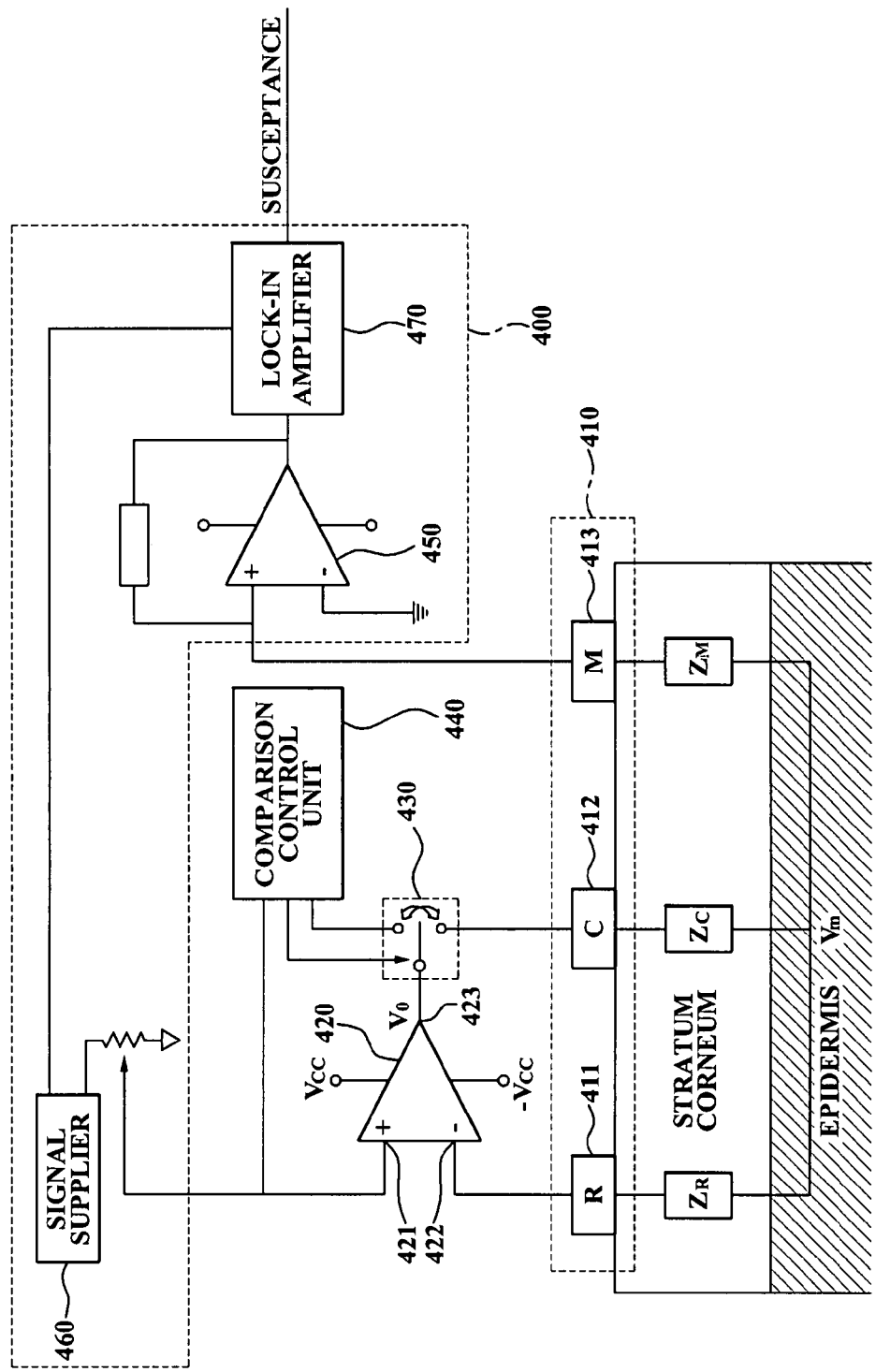
FIG. 4 is a circuit diagram illustrating a configuration of an apparatus for measuring skin moisture content according to an embodiment.

FIG. 4 is a circuit diagram illustrating a configuration of an apparatus for measuring skin moisture content according to an embodiment.

The apparatus for measuring skin moisture content according to the embodiment includes electrode units 411 through 413, an operation amplifier 420, a switch 430, a comparison control unit 440, a signal converter 450, a signal supplier 460, and a lock-in amplifier 470. In this specification, a signal converter 450, a signal supplier 460, and a lock-in amplifier 470 are together referred to as "measurement control module 400" for convenience of description.

The electrode unit 410 includes a reference (R) electrode 411, a current (C) electrode 412, and a measuring (M) electrode 413. The electrode unit 410 may be constructed to include the R electrode 411, the M electrode 412, and the C electrode 413. Also, the electrode unit 410 may be constructed to include any type of electrode that can measure the skin moisture content.

The operational amplifier 420 supplies the predetermined voltage to the electrode unit 410. To supply the voltage, an inverting terminal 422 of the operation amplifier 420 connects with the R electrode 411, and the output terminal 423 connects with the C electrode 412 via the switch. Also, a non-inverting input terminal 421 of the operational amplifier 420 connects with a comparison control unit 440.

Voltages Vcc and −Vcc may be supplied as a current source of the operational amplifier 420. When an input voltage $V_m$ of the operational amplifier 420 is supplied to the inverting terminal 422, the voltage $V_m$ may be supplied to the non-inverting input terminal 421 due to a virtual ground phenomenon.

Here, when the electrode unit 410 is contacted with the user's skin, a small current is generated in the non-inverting input terminal 421, and the voltage $V_m$ may be supplied to the user's epidermis layer. Skin resistance Zm varies depending on the user's skin moisture content. Accordingly, as the current detected through the M electrode 413 may be calculated as $I = V_m/Z_m$, the user's skin moisture content may be calculated in the formula described above.

Also, because the voltage at the R electrode 411 is floating towards 0V before the electrode unit 410 is contacted with the user's skin, the voltage at the C electrode 412 may be saturated at a voltage +Vcc. Here, because the voltage at the R electrode 411 becomes the voltage $V_m$ when the R electrode 411 is contacted with the user's skin before the C electrode 412, the voltage at the output terminal 423 of the operational amplifier 420 may be $2V_m$. Accordingly, assuming a general case that the switch 430 connects the operational amplifier 420 with the C electrode 412, the M electrode 413 may detect a current with an ordinary size via a voltage, i.e. $2V_m$ which is supplied to the C electrode 412.

However, when the C electrode 412 is contacted with the user's skin before the R electrode 411, the voltage at the R electrode 411 is 0V and the C electrode 412 is saturated at the voltage Vcc due to the current source and large current abruptly flows in the user's skin. Accordingly, assuming the general case that the switch 430 connects the operational amplifier 420 with the C electrode 412, a current signal, which is detected via the M electrode 413 due to the voltage Vcc at the C electrode 412, includes a noise having an abnormally large value and therefore, it is difficult to correctly measure the user's skin moisture content. A more specific description is given below with reference to FIG. 7 and FIG. 8.

Figure 7:
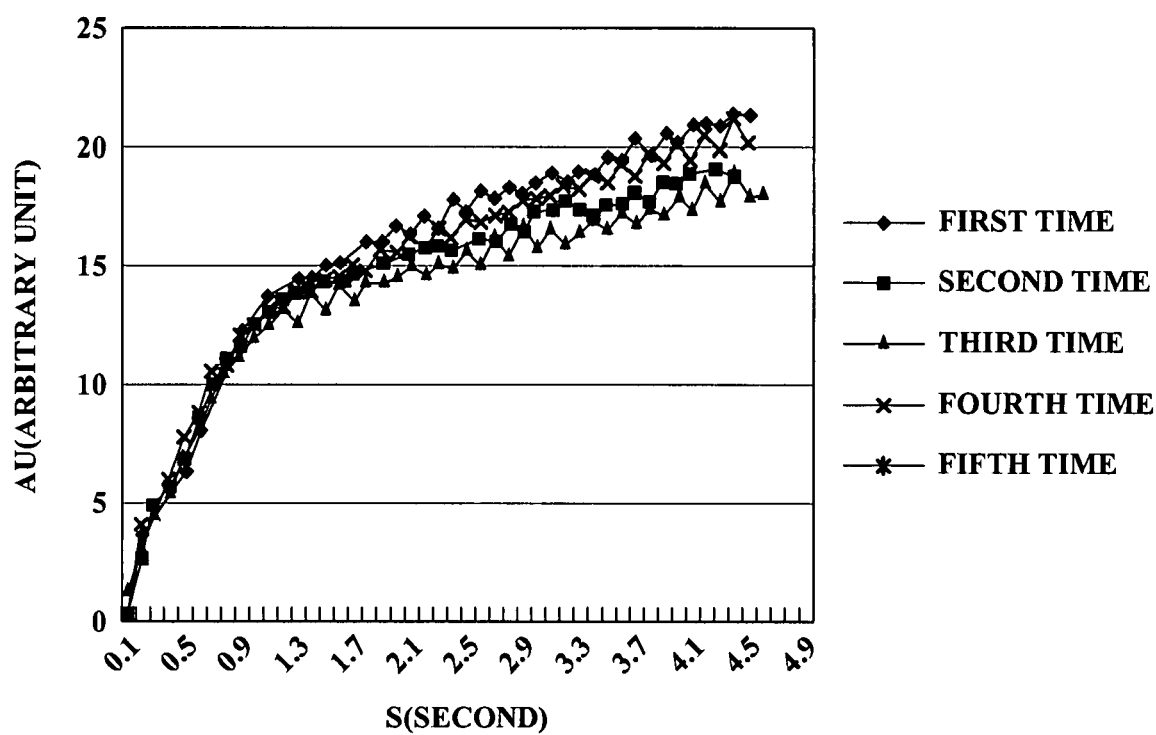
FIG. 7 is a diagram illustrating a graph of a measurement value of skin moisture content in a case when the R electrode is contacted with the user's skin before the C electrode according to an embodiment.

FIG. 7 is a diagram illustrating a graph of a measurement value of skin moisture content in a case when the R electrode is contacted with the user's skin before the C electrode according to an embodiment.

Figure 8:
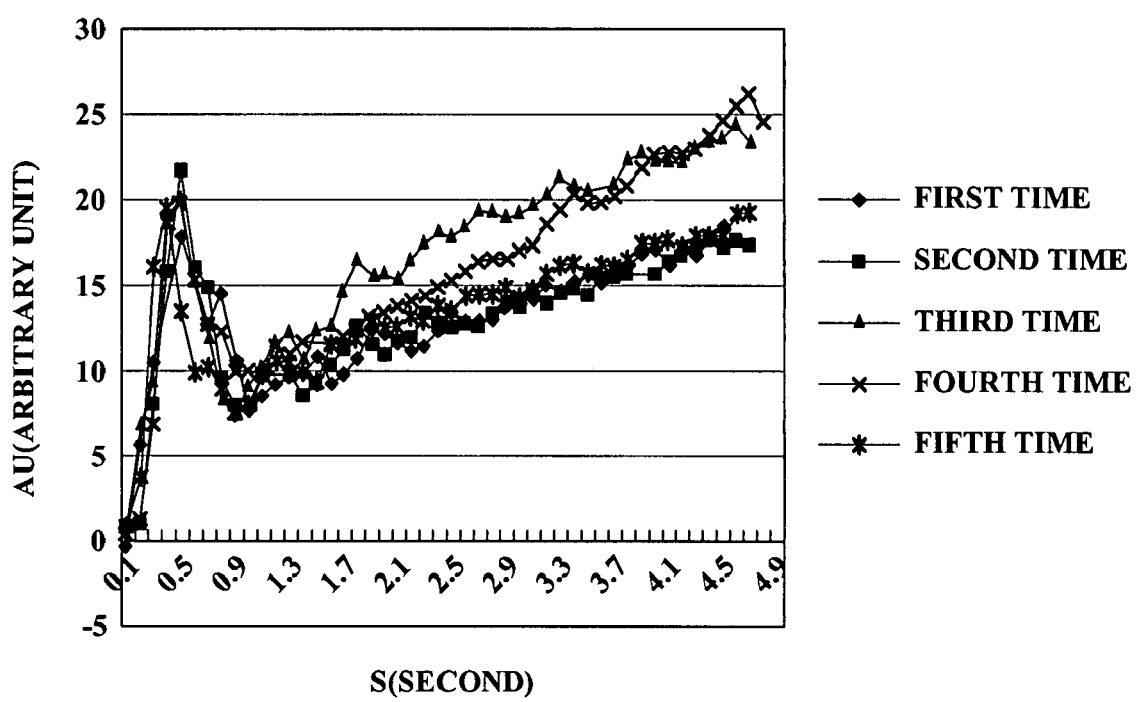
FIG. 8 is a diagram illustrating a graph of a measurement value of skin moisture content in a case when the C electrode is contacted with the user's skin before the R electrode according to an embodiment.

FIG. 8 is a diagram illustrating a graph of a measurement value of skin moisture content in a case when the C electrode is contacted with the user's skin before the R electrode according to another embodiment.

When the user's skin moisture content is measured from the current signal, which is detected from the M electrode 413, after the R electrode 411 is contacted with the user's skin before the C electrode 412, skin moisture content may be normally measured as illustrated in FIG. 7.

However, when the user's skin moisture content is measured after the C electrode 412 is contacted with the user's skin before the R electrode 411, the current detected from the M electrode 413 has an extraordinarily large value and a phenomenon in which a measured value instantaneously increases in the early stage of measurement as illustrated in FIG. 8. Here, when the R electrode 411 is contacted with the user's skin, the voltage at the C electrode 412 is restored to an originally stable value, for example, $2V_m$, after which skin moisture content may be normally measured as illustrated in a graph of FIG. 8.

As illustrated FIG. 7 and FIG. 8, when the R electrode 411 is contacted with the user's skin before the C electrode 412, skin moisture content may be quickly measured. However, when the C electrode 412 is contacted with the user's skin before the R electrode 411, skin moisture content may be normally measured after an abnormal section, which is generated in early stage of measurement, ends, and accordingly a problem in that it takes a long time to measure and accuracy is not assured, exists.

The apparatus for measuring skin moisture content according to an embodiment may include the switch 430, which is installed between the output terminal 423 of the operational amplifier 420 and the C electrode 412, and the comparison control unit 440 to prevent measurement mistakes which may occur due to an order of contact by the electrodes, of skin moisture content.

The switch 430 controls a connection between the output terminal 423 of the operational amplifier 420 and the C electrode 412. Specifically, the switch 430 may connect the output terminal 423 of the operational amplifier 420 with the C electrode 412, or connect the output terminal 423 with the comparison control unit 440. The switch 430 may connect the output terminal 423 with the C electrode 412 or the comparison control unit 440 depending on control of the comparison control unit 440.

The comparison control unit 440 compares a first voltage, which is supplied to the non-inverting input terminal 421 of the operational amplifier 420, with a voltage at the output terminal 423. Similar to the description above, when a first voltage $V_m$ is supplied to the inverting input terminal 422 of the operational amplifier 420, the voltage $V_m$ is supplied to the non-inverting input terminal 421 according to the virtual ground phenomenon. The comparison control unit 440 compares the voltage $V_m$, which is supplied to the non-inverting input terminal, with the voltage which is supplied to the output terminal 423.

When the voltage at the output terminal 423 is less than or equal to a value that is acquired by multiplying the voltage at the non-inverting input terminal 421 and a predetermined constant, the comparison control unit 440 controls the switch 430 to connect the output terminal 423 and the C electrode 412. The predetermined constant may be established in a gain value of the operational amplifier 420. For the convenience of description, a case when the predetermined constant is 2 is exemplified in the embodiment.

Before the electrode unit 410 is contacted with the user's skin or when the C electrode 412 is contacted with the user's skin before the R electrode 411, the output terminal 423 is saturated at the voltage Vcc similar to the description above. In this case, the voltage $V_o$ at the output terminal 423, is greater than the voltage $V_m$ at the non-inverting input terminal 421 and accordingly the comparison control unit 440 controls the switch not to connect the output terminal 423 and the C electrode 412. Specifically, the comparison control unit 440 may control the switch 430 to maintain a connection with the output terminal 423 or not.

Also, when the R electrode 411 is contacted with the user's skin before the C electrode 412, the voltage at the output terminal 423 may be $2V_m$ similar to the description above. The comparison control unit 440 compares the voltage at the output terminal 423 with a value that is acquired by multiplying the voltage $V_m$ at the non-inverting input terminal 421 and a predetermined constant, i.e. 2. Here, a value that is acquired by multiplying the voltage $V_m$ at the non-inverting input terminal 421 and a predetermined constant, i.e. 2, with the voltage at the output terminal 423 is the same and accordingly the comparison control unit 440 controls the switch 430 to connect the output terminal 423 and the C electrode 412. The user's skin moisture content may be measured by detecting the current signal, which is generated by an impedance of the user's stratum corneum, by connecting the output terminal 423 with the C electrode 412, via the detective M electrode 413.

Similarly, the comparison control unit 440 detects the current signal via the M electrode 413 by connecting the output terminal 423 with the C electrode 412 only when the voltage at the output terminal 423 terminal is less than or equal to a value that is acquired by multiplying the voltage at the non-inverting input terminal 421 and a predetermined constant, and thereby the skin moisture content may be accurately and consistently measured. Accordingly, the user is not required to ensure that the R electrode 411 is contacted with the skin before the C electrode 412 and may measure skin moisture content more conveniently and accurately.

Similarly, according to the apparatus for measuring skin moisture content of the embodiment, skin moisture content may be accurately measured according to control of the switch 430 by the comparison control unit 440 when the C electrode 412 is contacted with the user's skin before the R electrode 411. Specifically, when the C electrode 412 is contacted with the user's skin before the R electrode 411, the voltage at the output terminal 423 becomes greater than a voltage at the non-inverting input terminal 421, and accordingly the comparison control unit controls the switch so that the output terminal 423 is not connect the C electrode 412.

Then, when the C electrode 412 is initially contacted with the user's skin and the R electrode 411 is subsequently contacted with the user's skin, the voltage at the output terminal 423 is restored to an ordinary value similar to the description above. After the voltage at the output terminal 423 is restored to an ordinary value, the comparison control unit controls the switch 430 to connect the output terminal 423 with the C electrode 412. Accordingly, the user's skin moisture content may be accurately measured according to control of the switch 430, by the comparison control unit 440, even when the C electrode 412 is contacted with the user's skin before the R electrode 411 is contacted with the user's skin.

When the output terminal 423 and the C electrode 412 are connected via the switch 430, the signal converter 450 converts the current signal, which is detected via the M electrode 413, into a voltage signal. The signal converter 450 may include the operational amplifier to convert the current signal into the voltage signal.

The signal supplier 460 supplies the voltage signal by generating an out-phase signal to the lock-in amplifier 470. Specifically, the signal supplier 460 generates the out-phase signal to measure susceptance from the voltage signal and transmits the out-phase signal to the lock-in amplifier 470. The out-phase signal may be embodied in a cosine wave as a signal having a phase difference of 90° to the voltage signal. The signal supplier 440 may be embodied including the oscillator (not shown) to generate and supply the out-phase signal and the in-phase signal.

The lock-in amplifier 470 receives the voltage signal from the signal converter 450 and receives the out-phase signal from the signal supplier 460. The lock-in amplifier 470 measures susceptance of the current signal by synchronizing the voltage signal and the out-phase signal. The lock-in amplifier 470 may synchronize the out-phase signal and the voltage signal with each other by passing the voltage signal and the out-phase signal through a multiplier.

Similarly, the lock-in amplifier 470 may measure susceptance of the current signal by synchronizing the voltage signal and the out-phase signal. Also, the lock-in amplifier 470 may calculate information on the user's skin moisture content by using the above-measured susceptance.

Measuring skin moisture content may be implemented during a predetermined period of time, for example, 4 seconds. When measuring the skin moisture content is completed within the above-described period of time, the comparison control unit 440 may control the switch 430 to release the connection between the output terminal 423 and the C electrode 412.

The configuration and movement of the apparatus for measuring skin moisture content according to an embodiment have been described referring to FIG. 4. The apparatus for measuring skin moisture content according to an embodiment may include the switch 430 and the comparison control unit 440. The comparison control unit 440 may be embodied in a software module including a predetermined program to compare a value that is acquired by multiplying the voltage at the non-inverting input terminal 421 and a predetermined constant with the voltage at the output terminal 423, to control the switch 430.

According to another embodiment the comparison control unit 440 may be embodied in the predetermined hardware module. This is described referring to FIG. 5.

Figure 5:
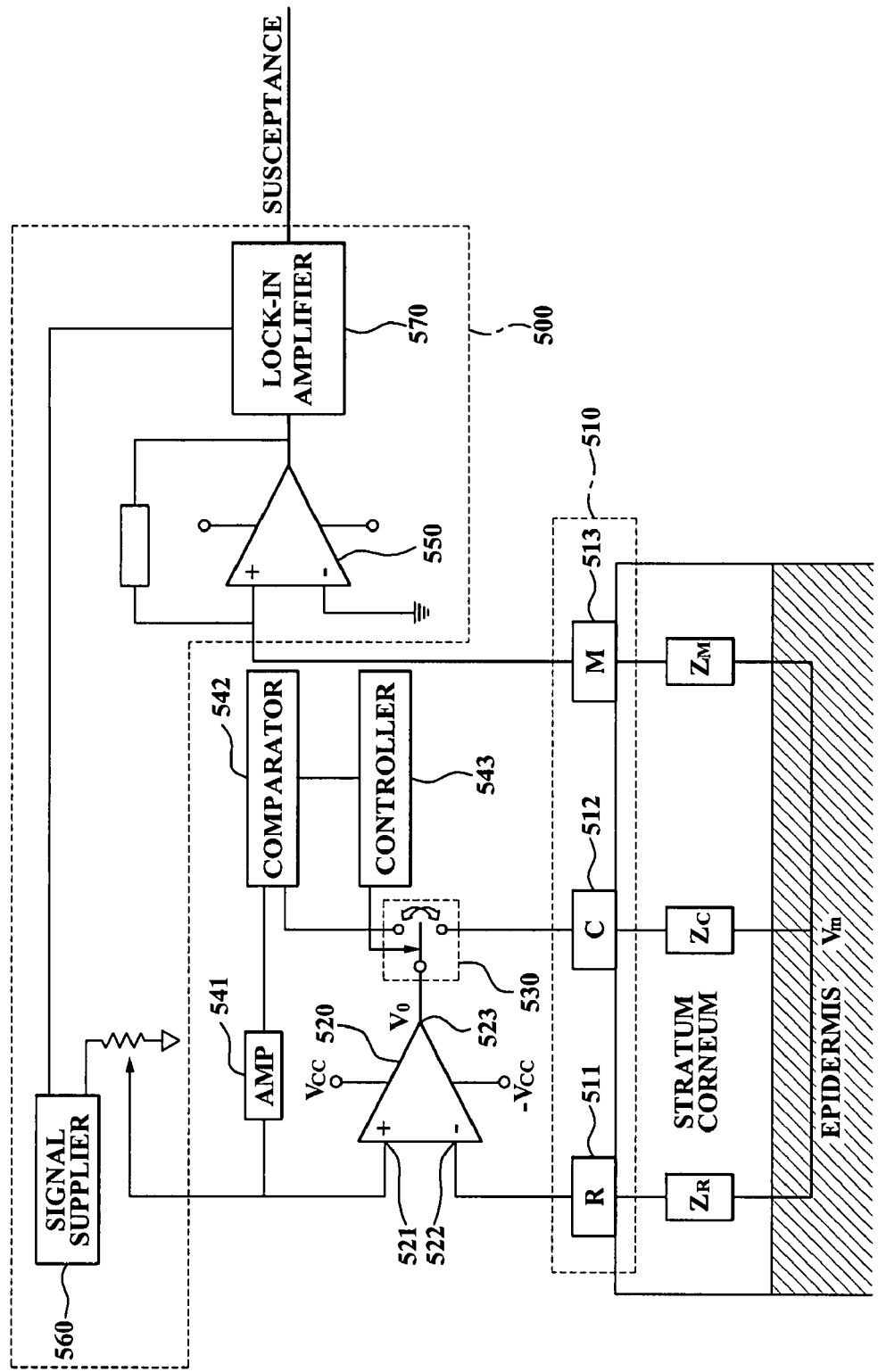
FIG. 5 is a circuit diagram illustrating a configuration of an apparatus for measuring skin moisture content according to another embodiment.

FIG. 5 is a circuit diagram illustrating a configuration of an apparatus for measuring skin moisture content according to another embodiment.

The apparatus for measuring skin moisture content according to the other embodiment may include an amplifier 541, a comparator 542, and a controller 543. Specifically, the comparison control unit 440 according to an embodiment may be embodied in the amplifier 541, the comparator 542, and the controller 543.

Accordingly, the amplifier 541 amplifies the voltage at the non-inverting terminal 521 to a value corresponding to a predetermined constant, and the comparator 542 compares an amplified voltage with the voltage at the output terminal 523. The controller 543 may control the connection between the output terminal 523 and the C electrode 512 via a switch 530 based on comparison result of the two voltages. As other configurations may be embodied in the same way as the configuration the apparatus for measuring skin moisture content according to an embodiment, detail description is omitted.

Figure 6:
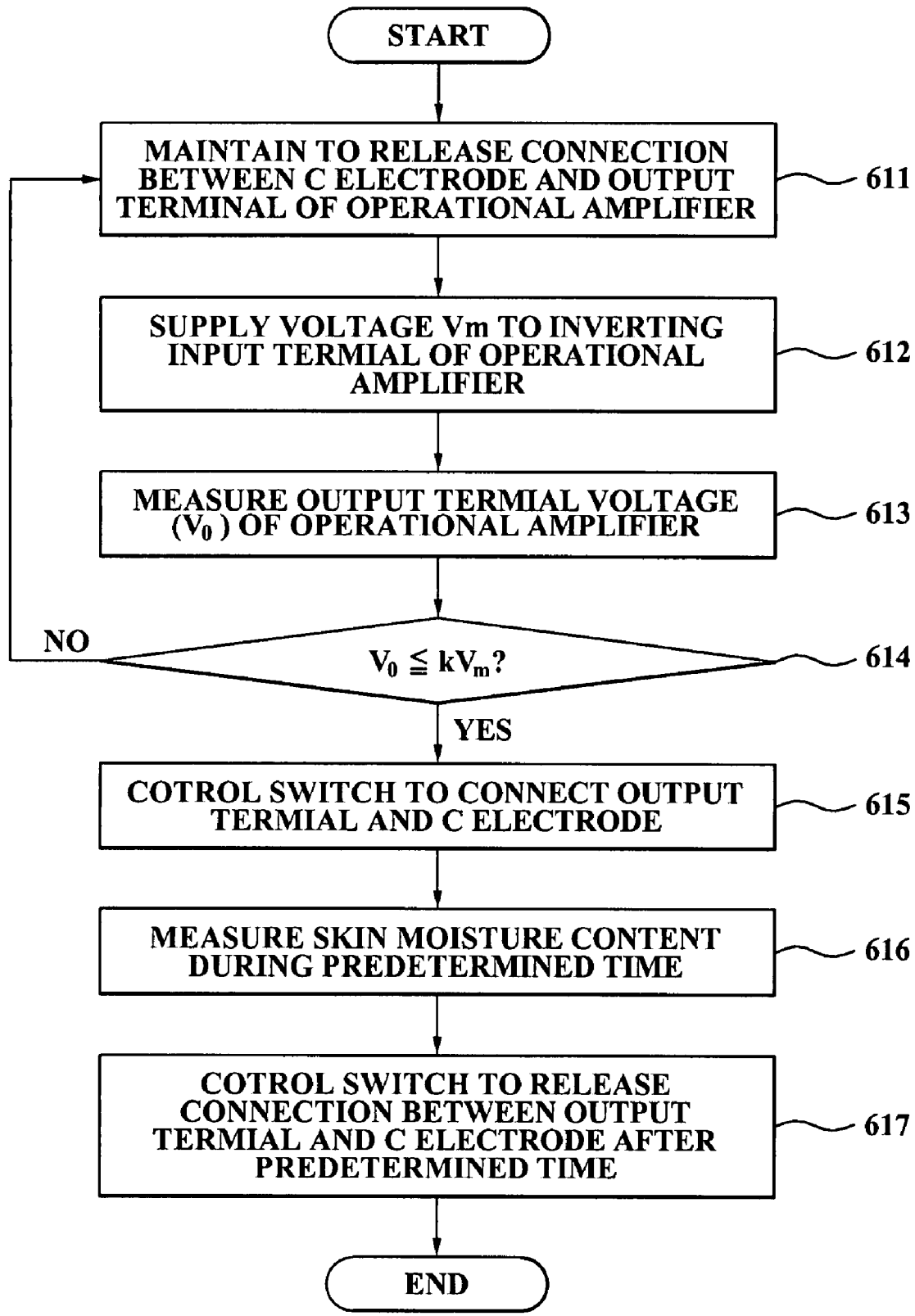
FIG. 6 is a flowchart illustrating a method of measuring skin moisture content according to an embodiment.

FIG. 6 is a flowchart illustrating a method of measuring skin moisture content according to the embodiment.

The method to measure skin moisture content according to the embodiment may be embodied in the apparatus for measuring skin moisture content including the R electrode, the C electrode, the M electrode and the operational amplifier as described with reference to FIGS. 4 and 5.

In operation 611, the apparatus for measuring skin moisture content controls the switch to release a connection between the C electrode and the output terminal of the operational amplifier when measuring skin moisture content is input from the user.

In operation 612, the apparatus for measuring the skin moisture content supplies a voltage $V_m$ to the inverting input terminal of the operational amplifier. When the voltage $V_m$ is supplied to the inverting input terminal, the voltage $V_m$ is supplied to the non-inverting input terminal of the operational amplifier as a result of a virtual ground phenomenon. In operation 613, the apparatus for measuring skin moisture content measures the voltage at the output terminal of the operational amplifier, i.e. V0.

Then, in operation 614, the apparatus for measuring the skin moisture content compares the voltage at the output terminal of the operational amplifier with a value that is acquired by multiplying the voltage $V_m$ at the non-inverting input terminal of the operational amplifier and a predetermined constant. When the voltage at the output terminal is greater than a value that is acquired by multiplying the voltage $V_m$ at the non-inverting input terminal and the predetermined constant as a result of comparison, the apparatus for measuring skin moisture content maintains a released condition of connection between the C electrode and the output terminal of the operational amplifier.

Also, as a result of the comparison in operation 614, when the voltage at the output terminal of the operational amplifier is less than or equal to a value that is acquired by multiplying the voltage $V_m$ at the non-inverting input terminal of the operational amplifier and the predetermined constant, the apparatus for measuring skin moisture content controls the switch to connect the output terminal and the C electrode in operation 615.

When the output terminal of the operational amplifier and the C electrode are connected, the apparatus for measuring skin moisture content detects the current signal generated by an impedance of the user's stratum corneum via the M electrode. The apparatus for measuring skin moisture content measures skin moisture content for a predetermined period of time by using the current signal and the out-phase signal in operation 616.

After the predetermined period of time, in operation 617, the apparatus for measuring skin moisture content controls the switch to release connection between the output terminal of the operational amplifier and the C electrode. Accordingly, the apparatus for measuring skin moisture content may accurately measure the user's skin moisture content during the predetermined period of time.

The method to measure skin moisture content according to the embodiment referring to FIG. 6 may be embodied including an operation of measuring the skin moisture content according to the configuration of the apparatus for measuring skin moisture content which has been described with reference to FIGS. 1 through 5.

Also, the method of measuring skin moisture content according to the above-described embodiment may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments.

According to the above-described embodiments, there is provided an apparatus for measuring skin moisture content and it's operation method, which can prevent measurement errors that may occur due to an order of contact by each electrode with the user's skin, by detecting noise that may occur when the electrodes contact with a the user's skin in an order of a reference (R) electrode, a current (C) electrode, and a measuring (M) electrode that contact with a user's skin, and measuring the user's skin moisture content when the occurrence of the noise disappears.

Also, according to the above-described embodiments, there is provided an apparatus for measuring skin moisture content and it's operation method, which can accurately measure skin moisture content by automatically selecting a point of measurement time while not inputting a starting time to measure skin moisture content, and by maintaining a predetermined measurement time while not installing another device such as a switch for informing the starting time, since skin moisture content is measured by detecting noise that occurs in an order of each electrode contacting with the skin.

Although a few exemplary embodiments have been shown and described, the embodiment is not limited to the described exemplary embodiments. Instead, it would be appreciated by those skilled in the art that changes may be made to these exemplary embodiments without departing from the principles and spirit of the invention, the scope of which is defined by the claims and their equivalents.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. An apparatus of measuring skin moisture content, the apparatus comprising:
    an electrode unit comprising a reference (R) electrode, a current (C) electrode, and a measuring (M) electrode;
    an operational amplifier comprising an inverting input terminal that is supplied with a first voltage and connects with the R electrode, and an output terminal that connects with the C electrode;
    a switch to control a connection between the output terminal and the C electrode; and
    a comparison control unit to compare the first voltage and a voltage at the output terminal, and controlling the switch to connect the output terminal and the C electrode when the voltage at the output terminal is less than or equal to a value that is acquired by multiplying the first voltage and a predetermined constant,
    wherein the comparison control unit controls the switch to release the connection between the output terminal and the C electrode when the voltage at the output terminal is greater than the value that is acquired by multiplying the first voltage and the predetermined constant.

2. The apparatus of claim 1, wherein the comparison control unit compares the first voltage that is supplied to a non-inverting input terminal of the operational amplifier, with the voltage at the output terminal, when the first voltage is supplied to the inverting input terminal of the operational amplifier.

3. The apparatus of claim 1, wherein the M electrode detects a current signal generated by an impedance in a user's skin stratum corneum when the output terminal and the C electrode are connected with each other.

4. The apparatus of claim 3, further comprising:
    a measurement control module to measure the user's skin moisture content using the current signal detected by the M electrode and a predetermined phase signal.

5. The apparatus of claim 4, wherein the measurement control unit comprises:
    a signal supplier;
    a lock-in amplifier to measure susceptance of the current signal; and
    signal converter the current signal to a voltage signal, wherein the signal supplier to supply an out-phase signal to the lock-in amplifier.

6. The apparatus of claim 5, wherein the out-phase signal is a cosign wave having a phase difference of 90 to the voltage signal.

7. The apparatus of claim 5, wherein the lock-in amplifier synchronizes the out-put phase signal and the voltage signal.

8. The apparatus of claim 1, wherein the comparison control unit controls the switch to release the connection between the output terminal and the C electrode after a predetermined time, the predetermined time corresponding to a time when the measurement control module measures the skin moisture content.

9. The apparatus of claim 1, wherein the predetermined constant corresponds to a gain value of the operational amplifier.

10. A method of measuring skin moisture content using a skin moisture content measurement apparatus comprising an R electrode, a C electrode, an M electrode, an operational amplifier, and a control unit, the method comprising:
    controlling, by the skin moisture content measurement apparatus, a switch to release a connection between an output terminal of the operational amplifier and the C electrode;
    supplying, by the skin moisture content measurement apparatus, a first voltage to an inverting input terminal of the operational amplifier;
    comparing, by the skin moisture content measurement apparatus, a value, acquired by multiplying the first voltage and a predetermined constant, with a voltage at the output terminal of the operational amplifier; and
    controlling, by the skin moisture content measurement apparatus, the switch to connect the output terminal and the C electrode when the voltage at the output terminal is less than or equal to the value that is acquired by multiplying the first voltage and the predetermined constant,
    controlling, by the skin moisture content measurement apparatus, the switch to release the connection between the output terminal and the C electrode when the voltage at the output terminal is greater than the value that is acquired by multiplying the first voltage and the predetermined constant.

11. The method of claim 10, further comprising:
    detecting, by the skin moisture content measurement apparatus, using the M electrode, a current signal generated by impedance in a user's skin stratum corneum when the output terminal and the C electrode are connected to each other;
    measuring, by the skin moisture content measurement apparatus, the user's skin moisture content during a predetermined time using the current signal and a predetermined phase signal; and
    controlling, by the skin moisture content measurement apparatus, the switch to release the connection between the output terminal and the C electrode after the predetermined time.

12. A computer-readable executable program product tangibly embodied on a computer readable recording medium having a computer-executable program, the computer-executable program executes the following:
    measuring skin moisture content using a skin moisture content measurement apparatus comprising an R electrode, a C electrode, an M electrode, an operational amplifier, and a control unit, wherein the measuring skin moisture content comprising:

controlling, by the skin moisture content measurement apparatus, a switch to release a connection between an output terminal of the operational amplifier and the C electrode;

supplying, by the skin moisture content measurement apparatus, a first voltage to an inverting input terminal of the operational amplifier;

comparing, by the skin moisture content measurement apparatus, a value, acquired by multiplying the first voltage and a predetermined constant, with a voltage at the output terminal of the operational amplifier;

controlling, by the skin moisture content measurement apparatus, the switch to connect the output terminal and the C electrode when the voltage at the output terminal is less than or equal to the value that is acquired by multiplying the first voltage and the predetermined constant; and controlling, by the skin moisture content measurement apparatus, the switch to release the connection between the output terminal and the C electrode when the voltage at the output terminal is greater than the value that is acquired by multiplying the first voltage and the predetermined constant.

13. A computer-readable executable program product of claim 12, wherein the measuring skin moisture content further comprising:

detecting, by the skin moisture content measurement apparatus, using the M electrode, a current signal generated by impedance in a user's skin stratum corneum when the output terminal and the C electrode are connected to each other;

measuring, by the skin moisture content measurement apparatus, the user's skin moisture content during a predetermined time using the current signal and a predetermined phase signal; and controlling, by the skin moisture content measurement apparatus, the switch to release the connection between the output terminal and the C electrode after the predetermined time.

* * * * *